United States Patent [19]

Voychehovski

[11] Patent Number: 4,906,234
[45] Date of Patent: Mar. 6, 1990

[54] MEDICAL TUBE HOLDER

[76] Inventor: Tomasz H. Voychehovski, 4754 Caldwell Mill Rd., Birmingham, Ala. 35243

[21] Appl. No.: 295,233
[22] Filed: Jan. 9, 1989
[51] Int. Cl.⁴ ........................................... A61M 25/02
[52] U.S. Cl. .................................. 604/79; 128/207.17
[58] Field of Search ......................... 604/79, 174, 179; 128/207.17, 207.18, DIG. 26

[56] References Cited

U.S. PATENT DOCUMENTS

| 2,590,006 | 3/1952 | Gordon | 128/206 |
| 3,946,742 | 3/1976 | Eross | 128/351 |
| 3,987,798 | 10/1976 | McGinnis | 128/351 |
| 4,392,857 | 7/1983 | Beran | 604/179 |
| 4,449,527 | 5/1984 | Hinton | 128/207.17 |
| 4,483,337 | 11/1984 | Clair | 128/207.17 |
| 4,530,354 | 7/1985 | Froilan | 128/207.17 |
| 4,622,034 | 11/1986 | Shattuck | 604/179 |
| 4,649,915 | 3/1987 | Heyden | 128/207 |
| 4,742,824 | 5/1988 | Payton et al. | 128/207.18 |

Primary Examiner—Stephen C. Pellegrino
Attorney, Agent, or Firm—Dann, Dorfman, Herrell & Skillman

[57] ABSTRACT

A holder for anchoring medical tubes which are used for providing access to hollow body organs. The holder consists of a band adapted to be adhesively secured to the face of the patient at three points. A series of receptacles is provided along the length of the band into which anchor elements may be selectively engaged. The anchor element supports the tube adjacent the band and anchors the tube against both lateral displacement and longitudinal displacement affecting the depth of penetration of the tube. The interconnection of the anchor with the band is facilitated by a quick-connect-disconnect arrangement provided by a plug portion on the anchor engaging in a complementary receptacle in the band.

19 Claims, 2 Drawing Sheets

1

MEDICAL TUBE HOLDER

FIELD OF THE INVENTION

The present invention relates to medical tubes for providing access to internal body organs and has Particular application to devices for holding and positioning endotracheal tubes in infants.

BACKGROUND OF THE INVENTION

The positioning and retaining of endotracheal tubes in infants is a troublesome problem in hospitals because of the need for displacement of the tube during care of the infant both by the nursing personnel and by the mother. Prior to the present invention, there has been no endotracheal tube holder which has been entirely satisfactory for use with infants.

In the care of infants, it is not only necessary to frequently attend to the cleaning and diapering of the infant, but also it is desirable to change the sleeping position of the infant so that the head of the infant is not adversely affected by prolonged periods in one position. Furthermore, the natural sucking response of the infant must be nurtured and parental bonding must be maintained during the care of the infant.

The most common practice in positioning and retaining endotracheal tubes is to simply use adhesive tape to anchor the tube adjacent the mouth and perhaps along the side of the face. The use of tape requires constant observation since the tape adjacent the mouth may lose its adhesion due to salivation or simply due to repeated mouth movement of the infant. Furthermore, the flexible nature of the tape permits undesired axial movement of the tube, which may affect the position of the internal tip of the tube in the body cavity. Normally, the positioning of the tip of the tube in the cavity is critical. Repeated removal and replacement of adhesive irritates the tender skin of the infant and without changing the position of the tube, there is a likelihood for creating a palatal groove in the infant.

Mechanical holders have been produced but such holders tend to be cumbersome and difficult to use and are generally not available in sizes appropriate for infants.

SUMMARY OF THE INVENTION

The present invention provides an improved holder for medical tubes which facilitates proper penetration of the tube end into the desired position in the body organ being accessed by the tube.

The present invention specifically provides a holder for holding an endotracheal tube suitable for use with infants.

In particular, the device provides a support band which may be mounted across the infant's face and left in place for prolonged periods without causing substantial discomfort or injury. An anchor is releasably attached to the band and may be adjusted therealong to enable repositioning of the tube within different areas of the oral cavity.

The band of the present invention enables mounting not only of the endotracheal tube but also other appliances or devices which may be desired.

The invention provides a holder which may be mounted in various positions on the band and in which the tube may be mounted for axial adjustment and anchoring so that the holder may be detached from the band for lateral adjustment without disturbing the axial adjustment of the tube in the holder, thereby maintaining the proper position of the internal tip of the tube.

In one embodiment of the invention, the tube is axially slidable in the holder and may be clamped at any desired position, and in another embodiment, the tube and holder are provided with screw threads which permit axial adjustment by rotation of the tube. In either case, calibrated indicia may be provided to enable both initial adjustment of the tube by use of the calibrations and to afford accurate repositioning in the event it is necessary to remove the tube from the holder.

The present invention provides adaptability of the equipment for various uses since the tube-holding devices are interchangeable with bands of various sizes and configurations. Thus, the apparatus of the present invention is readily adaptable to a wide range of circumstances.

BRIEF DESCRIPTION OF THE DRAWINGS

All of the objects of the invention are more fully set forth hereinafter with reference to the accompany drawings, wherein.

DESCRIPTION OF THE PREFERRED EMBODIMENTS

Figure 1:
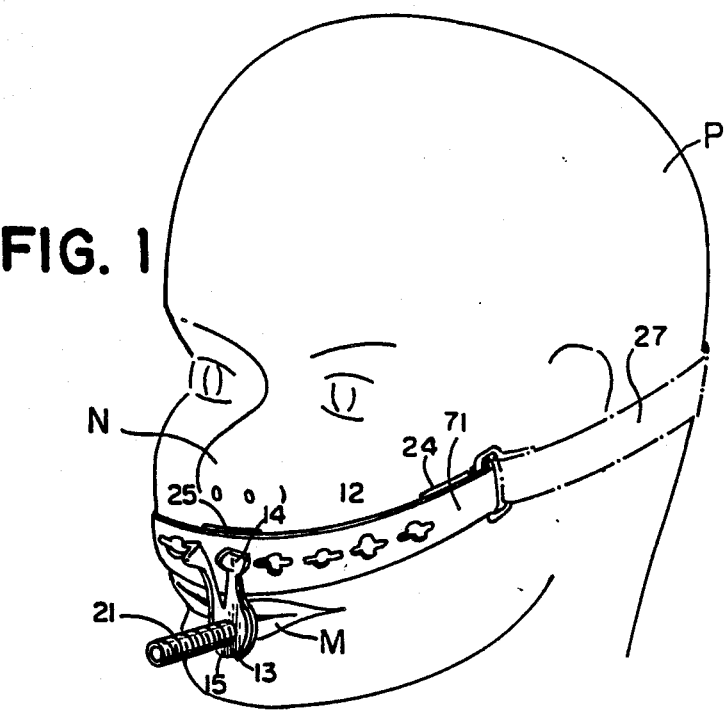
FIG. 1 is a view showing the application of the tube holder to an infant.
Figure 4:
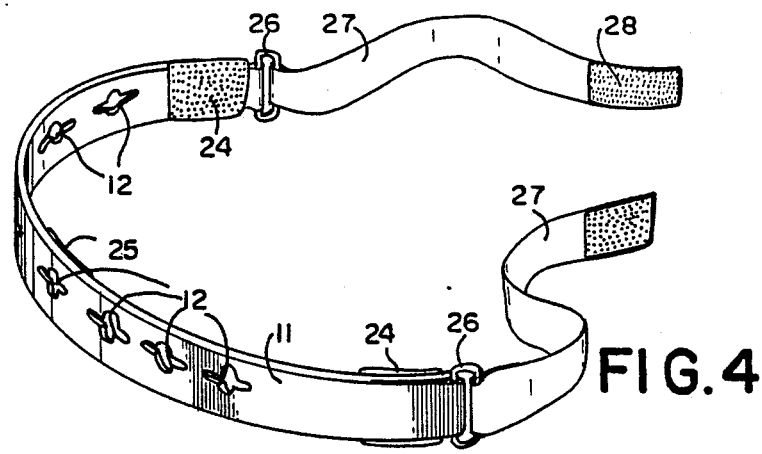
FIG. 4 is a view of the band removed from the head.

FIG. 1 illustrates a holder made in accordance with the present invention attached to the face of an infant P. The holder consists of a band 11 having a series of receptacles 12 positioned along the length of the band to receive an anchor element 13 consisting of a plug portion 14 and a collar portion 15. A medical tube, in the present instance an endotracheal tube 21, passes through the collar portion 15 and penetrates the mouth of the patient so that it may be projected into the proper position internally of the infant, for example in the lungs. As shown in FIG. 4, the band 11 is provided with adhesive pads 24,24 at its opposite ends and a similar medial pad 25 between the ends. The pads provide a flat land area which facilitates adhesive bonding of the band to the face of the patient.

As shown in FIG. 1, the band 11 extends across the full width of the face so that the end pads 24 are positioned in front of the ears in the temple area of the face. The band, in the present instance, follows the contour of the upper jaw and passes between the mouth M and the nose N of the patient so that the medial pad 25 engages the upper lip area between the upper lip of the mouth M and the nostril of the nose N. The pad may be a double-faced adhesive component which is separably mounted on the band 11 so as to permit the pad to be positioned in the upper lip area at a location which is most suitable for the particular infant. By following the line of the upper jaw between the temples, jowl movements of the patient do not adversely affect the adhesive bonding of the band 11 to the face of the patient through the pads 24 and 25. In the present instance, the pads have a noticeable thickness which enables the band between the pads to be spaced away from the face and permit air circulation beneath the band between the adhesively attached land areas provided by the pads 24 and 25.

The present invention permits a wide variety of band configurations which may be selected to conform to the dimensions of the individual patient. It is preferred that the band be supported at three points, namely at the temples and at a point adjacent the mouth, and the band is selected so as to enable this attachment.

In the present instance, the ends of the band 11 are provided with loops 26,26 to which a strap in the form of two segments 27,27 may be attached. The straps 27,27 may be wrapped behind the head of the patient secured together, for example by suitable fastening means 28, such as hook-and-loop patches, to hold the band in place before and during completion of the adhesive bond between the band and the face. Preferably, suitable adhesive is used in the adhesive bonding of the band to the face which permits the band to remain in place for prolonged periods. To facilitate care of the infant after the band is firmly adhered to the face, the straps may be removed, as indicated by the broken line in FIG. 1.

It is noted that the receptacles 12 are positioned at spaced intervals along the length of the band so that the anchor element 15 may be positioned in any one of the several receptacles in the series. Preferably, the receptacles are sufficiently close together to enable three or four of the receptacles to register with the mouth so that the anchor may be located at three or four different locations within the mouth. This permits the position of the tube in the mouth to be changed periodically to avoid palatal grooving. The receptacles remote from the mouth may be used for other attachments, such as tube guides, pacifiers, or other appliances which may be mounted near the face during the infant care. When the band is made of disposable material, the series of receptacles is co-extensive in length with the band so that when installing the band in the first instance, the proper length of band is simply cut from a continuous supply and it will have the necessary receptacles incorporated in it. The width of the band is preferably uniform throughout so that it may be universally used, but it may be desired to reduce the width of the band in the upper lip area, particularly where the spacing between the lip and the nostrils is small.

The anchor element 15 is designed to be easily and quickly attached to and detached from the band in any selected receptacle of the series. In the present instance, the receptacles comprise apertures through the entire thickness of the band, but it may be desired, particularly in narrow bands, to configure the receptacles in the form of blind recesses which are open on only the outer face of the band, the opposite face being continuous. Alternatively, the illustrated band may be provided with an interiorly-facing lining throughout its length without interfering with the desired quick-connect-and-disconnect engagement between the anchor 13 and the band 11.

Figure 5:
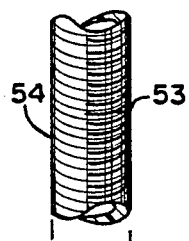
FIG. 5 shows an alternate anchor element in position for engagement with the band.
Figure 6:
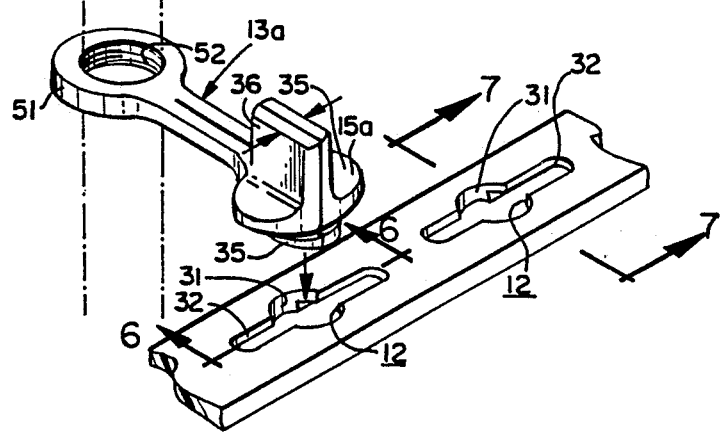
FIGS. 6 and 7 are fragmentary sectional views taken on the lines 6—6 and 7—7, respectively, of FIG. 5.
Figure 6:
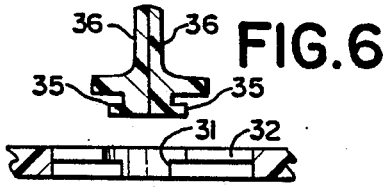
Figure 7:
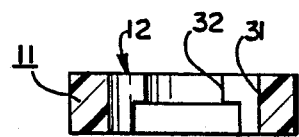

As shown in FIGS. 6 and 7, the receptacles 12 comprise an enlarged central opening 31 and a pair of diverging branches 32. The plug portion 14 of the anchor 13 comprises a pair of diverging prongs each having a base 35 and an upstanding finger tab 36. As shown in FIGS. 5 and 6, the branches 32 are undercut to provide for entrapment of the plug to prevent outward displacement when the bases 35 of the plug prongs are engaged in the branche. When mounting the anchor 13 into the receptacles 12, the finger tabs 36 are used to displace the prongs from the open position shown in FIGS. 1, 2 and 3 to the closed position shown in FIG. 5 so that the bases 35 may enter the receptacle 12 through the central opening 31. Upon release of the finger tabs 36, the resilience of the material forming the plug prongs causes the prongs to diverge and enter the diverging branches 32,32 of the receptacle 12. As shown in FIG. 6, the base is configured to interlock with the undercut part of the branch 32 so as to firmly engage the anchor 13 in the receptacle 12. The anchor 13 shown in FIGS. 2 and 3 has different collar arrangement than the anchor 13a shown in FIG. 5, but the plug prongs of the two forms of anchor are identical, and the same reference numerals have been used with respect to the plug components.

Figure 2:
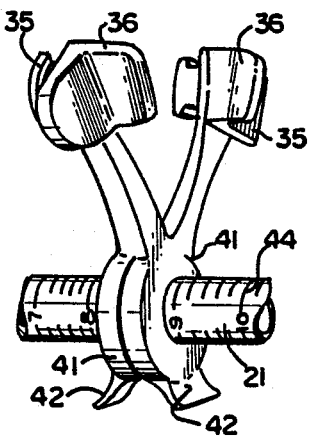
FIGS. 2 and 3 are perspective views showing a tube anchor separated from its band, FIG. 2 showing the position for axial adjustment of the tube and FIG. 3 showing the clamped position.
Figure 3:
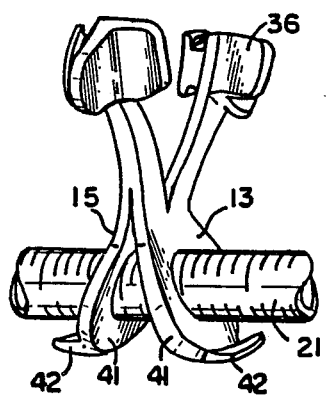

As shown in FIGS. 2 and 3, the collar 15 of the anchor 13 comprises a pair of rings 41,41 which are displaceable between the closed position shown in FIG. 2 wherein the rings are in face-to-face engagement, and the open position shown in FIG. 4 wherein the rings are open. In the closed position of FIG. 2, the rings are aligned with their central axes aligned so as to provide a clear through-passage which receives the tube 21 for free axial displacement therethrough. In the open position of FIG. 3, however, the rings are separated so that their axes are canted relative to one another and serve to frictionally engage the tube 21 and lock it against longitudinal movement. The openings through the rings 41,41 conform to the outer circumference of the tube 21, in the present instance both being cylindrical, and the anchor element is made of a resilient plastic material which permits the rings 41 to be displaced between their respective positions shown in FIGS. 2 and 3. The anchor is made of a resilient plastic material in the form shown in FIG. 3 so that when the rings are displaced from the position shown in FIG. 3 to the position shown in FIG. 2, the resilience of the plastic tends to return the rings to the clamping position of FIG. 3. To facilitate the displacement of the rings 41,41, each ring is provided with a finger tab 42.

In order to facilitate proper positioning of the tube with respect to its longitudinal penetration through the body opening, the tube 21 is provided with indicia 44 which enables measured longitudinal adjustment of the tube within the collar 15, and also provides a mechanism by which the depth of penetration of the tube through the body opening may be repeatedly returned to the desired setting. By the use of the indicia, the need for repeated fluoroscopic or x-ray inspection of the innermost tip of the tube is reduced. For example, the indicia may indicate the metric distance from the interior tip of the tube. Thus, the indicia may be used when replacing tubes to enable reasonably accurate positioning of the new tube to correspond to the previously determined proper position of the tube which it replaces.

An alternate collar arrangement is shown in FIG. 5 wherein the anchor 13a is provided with a collar 51. As shown in FIG. 5, the interior opening 52 of the collar conforms generally to outer circumference of the tube, which in FIG. 5 is designated 53. The collar opening 52 is internally threaded so as to engage the circumference of the tube 53. When the tube 53 is rotated about its longitudinal axis, the threads displace the tube longitudinally, depending upon whether the tube is rotated clockwise or counterclockwise. To enhance the threaded engagement between the tube 53 and the collar 51, the outer circumference of the tube 53 is threaded as indicated at 54. However, it should be noted that if the material of the tube is sufficiently soft, the internal threads of the collar 52 may be sufficient to provide a self-threading action on the outer circumference of the tube 53 without necessarily pre-forming the threads 54 in the tube 53. If desired, suitable indicia may be provided on the collar and the threaded tube to achieve the aforementioned desirability to properly reposition the tube after adjustments.

Normally, when the tube is removed temporarily and is later reintroduced, the interlocked engagement between the tube and the collar is not disturbed but, rather, the anchor 13 or 13a is simply disengaged from the receptacles 12 in the band to permit the withdrawal of the tube. Upon reinsertion, there is no need for adjustments since the engagement of the anchor in a receptacle will automatically reposition the tube in the proper location. The same situation exists when the position of the tube is changed by transferring the anchor from one receptacle to another within the mouth area.

While particular embodiments of the present invention have been herein illustrated and described, it is not intended to limit the invention to such disclosure, but changes and modifications may be made therein and thereto within the scope of the following claims.

I claim:

1. A holder for anchoring endotracheal tubes to the face of a patient comprising in combination:
    a supporting band having a length to extend across the full width of the face along the upper jaw of the patient between the ears, and a width, at least at its central portion, sufficiently narrow to fit between the nose and the upper lip of the patient, when the upper longitudinal edge is positioned adjacent the patient's nostrils and the lower longitudinal edge extends along the upper lip;
    a series of receptacles between the upper and lower edges positioned at spaced intervals along the length of said band; and
    an anchor element having plug means adapted to be selectively engaged in any one of the receptacles in said series and a collar portion to receive the endotracheal tube for positioning relative to the face;
    whereby said tube may be selectively anchored in any one of said series of receptacles along the length of said band.

2. A holder according to claim 1 wherein said collar portion comprises a pair of rings operable in a first position to receive said tube for free axial displacement therethrough, and operable in a second position to frictionally engage and clamp said tube and prevent axial displacement, said rings being biased toward said second position.

3. A holder according to claim 2 wherein each of said rings conforms to and slidably engages the outer circumference of said tube concentric with the central axis of the ring, in the first position the central axes of said rings being aligned and in the second position the central axes of said rings being canted.

4. A holder according to claim 2 wherein said anchor is formed of a resilient plastic material normally disposing said rings in said second position and operable to enable resilient displacement thereof into said first position.

5. A holder according to claim 4 including finger grips on each ring to facilitate displacement of said rings to said first position.

6. A older according to claim 1 wherein said collar comprises a ring having internal threads adapted to operatively engage the outer circumference of said tube, whereby upon rotation of said tube about its central axis, said threads effect axial displacement of said tube.

7. A holder according to claim 1 wherein said plug means is offset laterally from the central axis of said collar, so as to position said collar beyond an edge of said band when said plug means is engaged in one of said receptacle.

8. A holder according to claim 1 wherein each receptacle includes a central opening and a pair of diverging branches:
    said plug means comprising a pair of prongs normally disposed in an open diverging position and operable to be displaced into a closed compact position;
    in the closed position said prongs fitting freely within said central opening, and in the open position said prongs engaging in and being retained by said diverging branches;
    whereby said anchor may be freely engaged in and disengaged from said receptacles when said prongs are in said closed position, and said anchor is locked in its associated receptacle when said prongs are in said open position.

9. A holder according to claim 8 wherein said anchor is formed of a resilient plastic material normally disposing said prongs in said open position and operable to enable resilient displacement of said prongs into said closed position.

10. A holder according to claim 9 including finger grips on each prong to facilitate displacement of said prongs to said closed position.

11. A holder according to claim 1 wherein said band has end land areas adjacent each end adapted to confront the face of the patient adjacent the temples and a central land area adapted to confront the face of the patient adjacent to upper lip;
    said land areas providing sites for adhesive attachment of the band to the face at three widely-space points.

12. A holder according to claim 11 including a retaining strap engaging the band adjacent its ends and adapted to pass behind the head of the patient and retain the band in place before and/or during completion of the adhesive attachment of said land areas to the face 13. In combination with a medical tube which penetrates through an opening in the body of a patient to provide access to an internal organ, a holder for anchoring the tube to the body of a patient, comprising:
    a supporting band having a length to encircle the body adjacent said opening;
    at least one receptacle positioned along the length of said band; and
    an anchor element having plug means adapted to be selectively engaged in and disengaged from the receptacle and a collar portion to receive and engage the tube for positioning the tube relative to the opening;
    adjustable means to retain said tube in said anchor element and to adjustably retain the tube against longitudinal displacement, and to thereby positively locate the interior end of said tube at the proper site providing the desired access to said internal organ.

14. A combination according to claim 13 wherein said collar portion comprises a pair of elements adjustable to a first position to afford free longitudinal displacement of the tube through said collar and to a second position frictionally clamping said tube to said collar.

15. A combination according to claim 13 including indicia on said tube to indicate the longitudinal position of said tube in said collar and consequently the depth of penetration of said tube through said opening.

16. A combination according to claim 13 wherein said collar portion comprises a pair of rings operable in a first position to receive said tube for free axial displacement therethrough, and operable in a second position to frictionally engage and clamp said tube and prevent axial displacement, said rings being biased toward said second position.

17. A combination according to claim 16 wherein each of said rings conforms to and slidably engages the outer circumference of said tube concentric with the central axis of the ring, in the first position the central axes of said rings being aligned and in the second position the central axes of said rings being canted.

18. A combination according to claim 17 wherein said anchor is formed of a resilient plastic material normally disposing said rings in said second position and operable to enable resilient displacement thereof into said first position.

19. A combination according to claim 13 wherein said collar portion is internally threaded, and said tube is externally threaded whereby longitudinal adjustment of said tube is effected by rotation of said tube relative to said collar.

* * * * *